United States Patent [19]

Nohira et al.

[11] Patent Number: 4,867,903
[45] Date of Patent: Sep. 19, 1989

[54] FLUOROALKANE DERIVATIVE

[75] Inventors: Hiroyuki Nohira; Masanao Kamei; Shinichi Nakamura, all of Urawa; Kazuharu Katagiri, Tama, all of Japan

[73] Assignee: Canon Kabushiki Kaisha, Tokyo, Japan

[21] Appl. No.: 22,928

[22] Filed: Mar. 6, 1987

[30] Foreign Application Priority Data

Mar. 10, 1986 [JP] Japan .................................. 61-50583
Dec. 4, 1986 [JP] Japan .................................. 61-287730

[51] Int. Cl.$^4$ ..................... C09K 19/34; C09K 19/30; C09K 19/12; C09K 19/20; C07C 69/76; C07C 69/773; C07D 239/26
[52] U.S. Cl. ........................ 252/299.61; 252/299.01; 252/299.5; 252/299.6; 252/299.63; 252/299.65; 252/299.66; 252/299.67; 350/350 R; 350/350 S; 544/242; 544/296; 544/298; 544/315; 544/318; 544/335; 560/59; 560/60; 560/61; 560/64; 560/55; 560/73; 560/102; 560/109; 560/111; 560/116; 560/117; 560/118; 560/126; 560/1; 560/8; 568/642; 568/647; 568/655; 568/661; 568/664; 568/669
[58] Field of Search .......... 252/299.01, 299.5, 299.61, 252/299.63, 299.64, 299.65, 299.66, 299.67, 299.6; 250/250 R, 250 S; 544/242, 296, 298, 315, 318, 335; 560/54, 60, 61, 64, 55, 73, 102, 109, 111, 116, 117, 118, 126, 1, 8; 568/642, 647, 655, 661, 664, 669

[56] References Cited

U.S. PATENT DOCUMENTS

| | | | |
|---|---|---|---|
| 4,576,732 | 3/1986 | Isogai et al. | 252/299.67 |
| 4,592,858 | 6/1986 | Higuchi et al. | 252/299.66 |
| 4,596,667 | 6/1986 | Inukai et al. | 252/299.67 |
| 4,613,209 | 9/1986 | Goodby et al. | 252/299.01 |
| 4,614,609 | 9/1986 | Inoue et al. | 252/299.66 |
| 4,615,586 | 10/1986 | Geary et al. | 252/299.01 |
| 4,695,650 | 9/1987 | Walba et al. | 252/299.01 |
| 4,695,651 | 9/1987 | Higuchi et al. | 252/299.66 |
| 4,697,015 | 9/1987 | Kano et al. | 252/299.61 |
| 4,713,197 | 12/1987 | Eidenschink et al. | 252/299.61 |
| 4,725,688 | 2/1988 | Taguchi et al. | 252/299.61 |
| 4,728,458 | 3/1988 | Higuchi et al. | 252/299.67 |
| 4,732,699 | 3/1988 | Higuchi et al. | 252/299.66 |
| 4,764,636 | 8/1988 | Sasaki et al. | 252/299.61 |
| 4,798,680 | 1/1989 | Nohira et al. | 252/299.01 |

FOREIGN PATENT DOCUMENTS 174816 3/1986 European Pat. Off. ....... 252/299.66

(List continued on next page.)

OTHER PUBLICATIONS

Goodby, J. W. et al., J. Am. Chem. Soc., vol. 108, pp. 4729–4735 (Aug. 6, 1986).
Goodby, J. W. et al., Liquid Crystals and Ordered Fluids, vol. 4, Griffin, A., Ed., Plenum Press, N.Y., pp. 1–32 (1985).
Patent Abs. JP, vol. 11, No. 30 (1987).

Primary Examiner—Teddy S. Gron
Attorney, Agent, or Firm—Fitzpatrick, Cella, Harper & Scinto

[57] ABSTRACT

A fluoroalkane derivative represented by the formula:

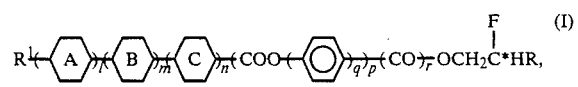

wherein R denotes an alkyl group having 1–16 carbon atoms, C* denotes an asymmetric carbon atom, $R^1$ denotes an alkyl or alkoxy group having 1–16 carbon atoms;

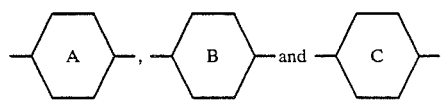

respectively denote a phenylene group

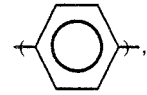

a cyclohexylene group

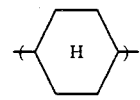

or a pyrimidinylene group

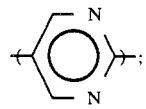

p is 0 or 1, q is 0 or 1 when p is 1, r is 0 or 1; and l, m and n are respectively 0 or a positive integer satisfying the relationship of $l+m+n \geq 1$. The fluoroalkane derivative has a fluorine atom providing a large dipole moment and directly connected to an asymmetric carbon atom, so that it provides a high speed responsive characteristic through an increased spontaneous polarization when contained in a liquid crystal composition, especially a ferroelectric liquid crystal composition.

45 Claims, No Drawings

FOREIGN PATENT DOCUMENTS

| | | | |
|---|---|---|---|
| 191600 | 8/1986 | European Pat. Off. | 252/299.67 |
| 225195 | 6/1987 | European Pat. Off. | 252/299.61 |
| 248335 | 12/1987 | European Pat. Off. | 252/299.61 |
| 3404116 | 8/1985 | Fed. Rep. of Germany | 252/299.61 |
| 3525015 | 1/1986 | Fed. Rep. of Germany | 252/299.66 |
| 3515373 | 11/1986 | Fed. Rep. of Germany | 252/299.61 |
| 3515374 | 11/1986 | Fed. Rep. of Germany | 252/299.61 |
| 3518734 | 11/1986 | Fed. Rep. of Germany | 252/299.61 |
| 59-157056 | 9/1984 | Japan | 252/299.63 |
| 59-219251 | 12/1984 | Japan | 252/299.65 |
| 200972 | 9/1986 | Japan | 252/299.01 |
| 61-200972 | 9/1986 | Japan | 252/299.61 |
| 86/00087 | 1/1986 | World Int. Prop. O. | 252/299.61 |
| 86/06401 | 11/1986 | World Int. Prop. O. | 252/299.61 |
| 87/05012 | 8/1987 | World Int. Prop. O. | 252/299.01 |
| 87/05012 | 8/1987 | World Int. Prop. O. | 252/299.01 |
| 87/05018 | 8/1987 | World Int. Prop. O. | 252/299.01 |

FLUOROALKANE DERIVATIVE

FIELD OF THE INVENTION AND RELATED ART

The present invention relates to a novel mesomorphic compound and, more particularly, to an optically active mesomorphic compound, a chiral smectic liquid crystal composition containing the same and a liquid crystal device using the liquid crystal composition.

There has been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127–128. In this type of liquid crystal devices, the number of picture elements have been restricted, because there is a problem that a crosstalk phenomenon occurs when a device of a matrix electrode structure with a high density of picture elements is driven according to a multiplexing driving scheme. Further, their uses for display have been limited because of slow electric field response and poor visual angle characteristics.

As another type of liquid crystal device, there has been known one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924). As the bistable liquid crystal, a ferroelectric liquid crystal showing a chiral smectic C phase (SmC*) or H phase (SmH*) is generally used.

Such a ferroelectric liquid crystal has very rapid response speed on account of having spontaneous polarization, can also exhibit memorizable bistable state and further have excellent vision angle characteristic, and therefore it is suitable for a display of large capacity and large picture area.

Further, since a material used as a ferroelectric liquid crystal has an asymmetry, it can be used as a functional material to be used in the following types of optical devices in addition to the use as a ferroelectric liquid crystal material:

(1) Those utilizing a cholesteric-nematic phase transition in a liquid crystal state (J. J. Wysoki, A. Adams and W. Haas: Phys. Rev. Lett., 20, 10204 (1968);

(2) Those utilizing a guest-host effect of the White-Taylor type in a liquid crystal state (D. L. White and G. N. Taylor: J. Appl. Phys. 45, 4718 (1974)).

These optical devices are important as display devices and modulation devices, while the explanation of the individual systems is left to the respective references and omitted.

It has been understood that, in a method utilizing an electric field-responsive optical effect of a liquid crystal, it is desirable to introduce a polar group or a group providing a polar bond in a compound constituting the liquid crystal in order to enhance the responsive characteristic of the liquid crystal. Particularly, with respect to a ferroelectric liquid crystal, it has been known that the responsive speed is proportional to its spontaneous polarization, so that it is desired to increase the spontaneous polarization in order to realize a high response speed. From this viewpoint, P. Keller et al have shown that it is possible to provide a higher response speed by introducing a chlorine atom directly connected to an asymmetric carbon atom. However, such a chlorine atom directly introduced to an asymmetric carbon atom involves problems that it is chemically unstable and lowers the stability of a liquid crystal phase as it has a large atomic radius.

On the other hand, many of optically active functional compounds for use in optical devices as described above are synthesized through an intermediate which per se is optically active. Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives However, it has been seldom to incorporate a polar group into such an intermediate. Partly for this reason, the above mentioned method of introducing a polar group directly to an asymmetric carbon atom has not been utilized very effectively.

SUMMARY OF THE INVENTION

A principal object of the present invention is, in view of the above problems, to provide a mesomorphic compound having an enhanced electric field-responsive characteristic in an liquid crystal state by introducing a fluorine atom, which is stable and has a large dipole moment, directly to an asymmetric carbon atom.

Another object of the present invention is to provide a liquid crystal composition comprising at least one species of the mesomorphic compound.

A further object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226, 146 (1964), and a liquid crystal composition containing at least one species of the mesomorphic compound.

According to the present invention, there is provided a fluoralkane derivative represented by the formula:

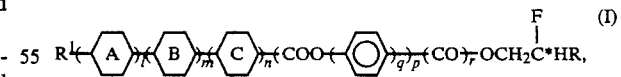

wherein R denotes an alkyl group having 1–16 carbon atoms, C* denotes an asymmetric carbon atom, $R^1$ denotes an alkyl or alkoxy group having 1–16 carbon atoms;

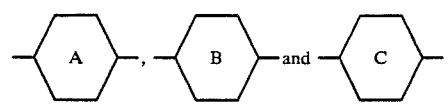

respectively denote a phenylene group

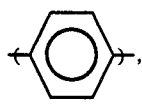

a cyclohexylene group

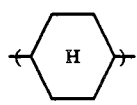

or a pyrimidinylene group

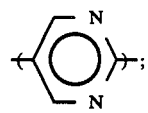

p is 0 or 1, q is 1 or 2 when p is 1, r is 0 or 1; and l, m and n are respectively 0 or a positive integer satisfying the relationship of $l+m+n \vee 1$.

According to the present invention, there is further provided a liquid crystal composition containing at least one species of the above mentioned optically active fluoroalkane derivative These and other objects, features and advantages of the present invention will become more apparent upon a consideration of the following description of the preferred embodiments of the present invention taken in conjunction with the accompanying drawings.

DETAILED DESCRIPTION OF THE INVENTION

The optically active fluoroalkane derivative represented by the above formula (I) may be synthesized from optically active intermediates such as 2-fluoro-1-alkanols, 2-fluoroalkyl, p-hydroxybenzoates, 2-fluoroalkyl p-hydroxybiphenylcarboxylates, hydroquinone 2-fluoroalkyl ethers, and 4-[4'-(2-fluoroalkyl)oxyphenyl]-phenol.

For example, the mesomorphic compound represented by the formula (I) may be synthesized from these optically active intermediates through reaction paths as shown below.

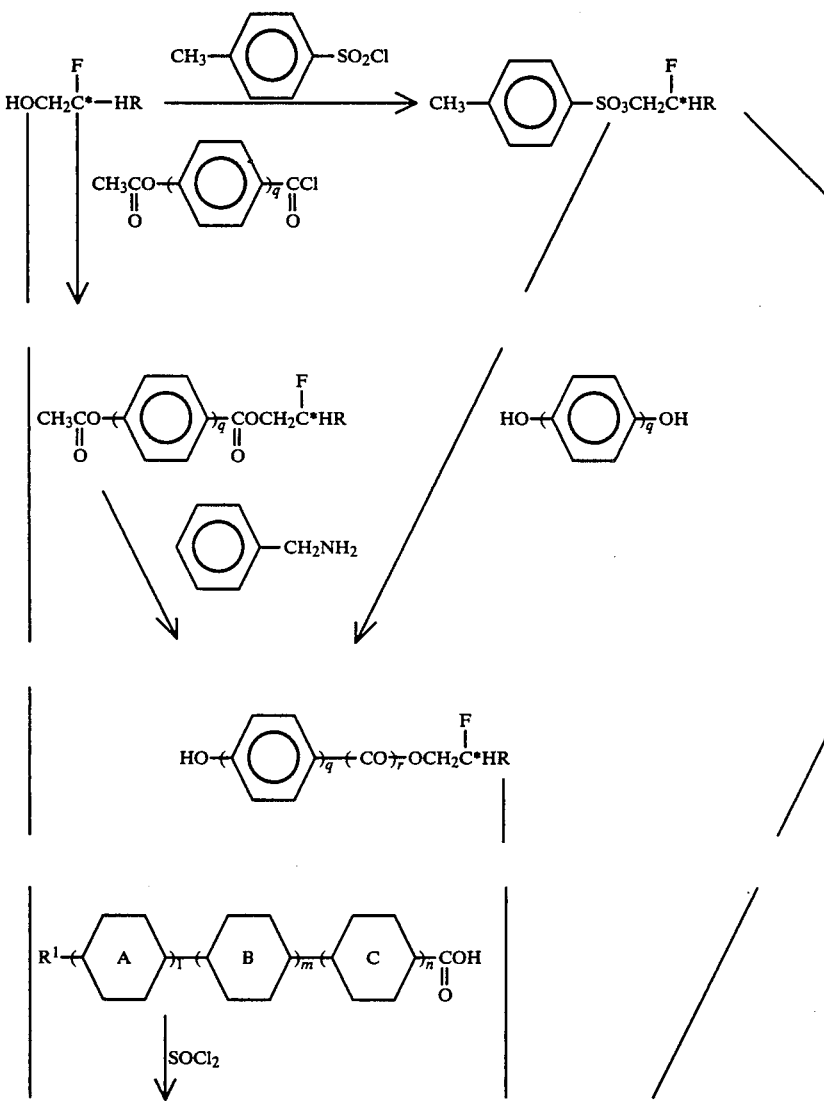

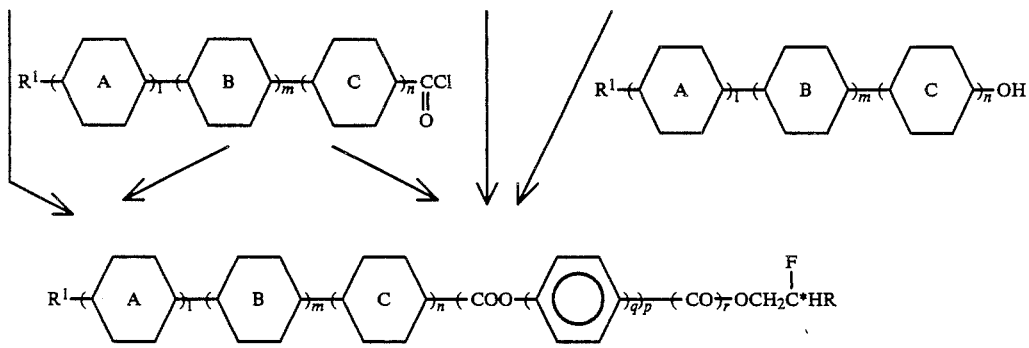

(In the above, the symbols R, R¹

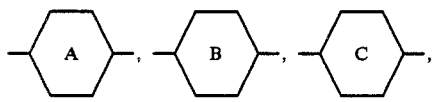

p, q, r, l, m and n have the meanings as defined above.)

In the following Table 1 are shown some examples of the fluoralkane derivatives produced in the manner as shown above together with their optical rotations and phase transition characteristics. The details of production will be explained in the Examples appearing hereinafter.

In the Table and the description appearing hereinafter, the symbols used for describing phase-transition respectively denote the following phases.
  Cryst crystal phase,
  SmA: smectic A phase,
  SmC*: chiral smectic phase,
  N: nematic phase,
  Ch: cholesteric phase,
  Iso.: isotropic phase,
  SmA: smectic A phase,
  SmB: smectic B phase, and
  Sm3: smectic phase (un-identified) other than SmA and SmC*.

TABLE 1

| Example | R | R¹ | l | A | m | B | n | C | p | q | r | Optical rotation [α]$_D$ | Phase transition temperature (°C.) |
|---|---|---|---|---|---|---|---|---|---|---|---|---|---|
| 1 | $C_6H_{13}$— | $C_8H_{17}O$— | 2 | phenyl | 0 | — | 0 | — | 0 | 0 | 1 | +13.1° (26.4° C.) c = 2, benzene | Cryst. ⇌ 95.2/85.2 Iso. |
| 2 | $C_6H_{13}$— | $C_{10}H_{21}O$— | 2 | phenyl | 0 | — | 0 | — | 0 | 0 | 1 | +12.3° (28.4° C.) c = 1, benzene | Cryst. ⇌ 92.3/85.0 Iso. |
| 3 | $C_5H_{11}$— | $C_8H_{17}$— | 1 | pyridyl (N) | 1 | phenyl | 0 | — | 0 | 0 | 0 | +0.44° (25.6° C.) c = 0.91, CHCl₃ | Cryst. ⇌ 25.4/−3.4 SmA ⇌ 41.5/23.0 Iso. |
| 4 | $C_6H_{13}$— | $C_8H_{17}$— | 1 | pyridyl (N) | 1 | phenyl | 0 | — | 0 | 0 | 0 | +0.21° (22.0° C.) c = 1, CHCl₃ | Cryst. ⇌ 61.5/44.8 Iso., Cryst. → SmA → Iso. 58.5 |
| 5 | $C_8H_{17}$— | $C_7H_{15}$— | 1 | pyridyl (N) | 1 | phenyl | 0 | — | 0 | 0 | 1 | +10.4° (23.2° C.) c = 2, benzene | Cryst. ⇌ 70.3/58.6 Iso. |
| 6 | $C_7H_{15}$— | $C_{10}H_{21}O$— | 2 | phenyl | 0 | — | 0 | — | 1 | 1 | 1 | +6.31° (27.6° C.) c = 1, benzene | Cryst. ⇌ 105.4/80.4 SmC* ⇌ 152.9/151.0 SmA ⇌ 178.3/176.0 Iso., Sm3 94.4 |
| 7 | $C_6H_{13}$— | $C_8H_{17}$— | 2 | phenyl | 0 | — | 0 | — | 1 | 1 | 1 | +8.7° (26.4° C.) c = 2, benzene | Cryst. ⇌ 107.7/70.5 SmC* ⇌ 185.3/183.0 SmA ⇌ 188.2/185.1 Iso., Sm3 81.1 |

TABLE 1-continued

| Example | R | R¹ | A | m | B | n | C | p | q | r | Optical rotation $[\alpha]_D$ | Phase transition temperature (°C.) |
|---|---|---|---|---|---|---|---|---|---|---|---|---|
| 8 | $C_8H_{17}$— | $C_7H_{15}$— | pyrazine | 1 | benzene | 0 | — | 1 | 1 | 0 | −2.8° (22.0°) c = 1, benzene | Cryst. $\xrightarrow{88.1}_{61.3}$ SmA $\xrightarrow{141.8}_{139.7}$ Ch $\xrightarrow{155.7}_{153.5}$ Iso. |
| 9 | $C_8H_{17}$— | $C_{10}H_{21}O$— | benzene | 0 | — | 0 | — | 1 | 1 | 0 | +0.6° (22.4° C.) c = 0.98, CHCl₃ | Cryst. $\xrightarrow{120.4}$ SmC* $\xrightarrow{175.0}_{172.8}$ SmA $\xrightarrow{191.7}_{188.9}$ Iso.; Sm3 115.4, 103.2 |
| 10 | $C_6H_{13}$— | $C_8H_{17}O$— | benzene | 0 | — | 0 | — | 1 | 2 | 0 | −3.0° (16.0° C.) c = 1, benzene | Cryst. $\xrightarrow{130.6}_{109.3}$ SmC* $\xrightarrow{172.6}_{169.8}$ Ch $\xrightarrow{193.2}_{190.5}$ Iso. |
| 11 | $C_8H_{17}$— | $C_8H_{17}O$— | benzene | 0 | — | 0 | — | 1 | 1 | 0 | −1.5° (23.2° C.) c = 0.94, benzene | Cryst. $\xrightarrow{70.1}_{55.5}$ SmC* $\xrightarrow{76.8}_{76.2}$ SmA $\xrightarrow{84.3}_{82.4}$ Ch $\xrightarrow{87.1}_{84.9}$ Iso. |
| 12 | $C_8H_{17}$— | $C_8H_{17}O$— | benzene | 0 | — | 0 | — | 1 | 1 | 0 | +8.7° (22° C.) c = 1, benzene | Cryst. $\xrightarrow{64.8}_{40.2}$ Iso. 59.9 SmA |
| 13 | $C_8H_{17}$— | $C_7H_{15}$— | cyclohexane | 1 | pyrimidine | 1 | benzene | 0 | 0 | 1 | +11.6° (18° C.) c = 1, benzene | Cryst. $\xrightarrow{71.8}_{29.1}$ Iso. |
| 14 | $C_6H_{13}$— | $C_{12}H_{25}O$— | benzene | 0 | — | 0 | — | 1 | 1 | 0 | −2.8° (22.0° C.) c = 1, benzene | Cryst. $\xrightarrow{83.6}$ SmA $\xrightarrow{92.3}_{89.6}$ Iso.; 83.1 SmA* 64.2 Sm3 54.7 |

TABLE 1-continued

| Example | R | R¹ | l | A | m | B | n | C | p | q | r | Optical rotation $[\alpha]_D$ | Phase transition temperature (°C) |
|---|---|---|---|---|---|---|---|---|---|---|---|---|---|
| 15 | $C_{12}H_{25}$— | $C_6H_{13}O$— | 1 | ⬡ | 0 | — | 0 | — | 1 | 1 | 0 | −1.5° (19.6° C.) c = 2, benzene | Cryst. $\xrightarrow{81.4}_{69.1}$ Ch $\xrightarrow{}_{74.1}$ Iso. |
| 16 | $C_6H_{13}$— | $C_8H_{17}O$— | 1 | ⬡ | 0 | — | 0 | — | 1 | 2 | 1 | +5.9° (21° C.) c = 1, $CH_2Cl_2$ | Cryst. $\xrightarrow{108.4}_{97.4}$ SmC* $\xrightarrow{104.2}_{109.6}$ SmA $\xrightarrow{171.2}_{169.6}$ Ch $\xrightarrow{173.2}_{171.7}$ Iso., Sm3 $\xrightarrow{140.1}$ |
| 17 | $C_5H_{11}$— | $C_{10}H_{21}O$— | 1 | ⬡ | 0 | — | 0 | — | 1 | 1 | 0 | +2.0° (20° C.) c = 1, $CH_2Cl_2$ | Cryst. $\xrightarrow{78.1}_{53.2}$ SmA $\xrightarrow{86.8}_{85.0}$ Iso., SmC* $\xrightarrow{64.0}$ |
| 18 | $C_6H_{13}$— | $C_8H_{17}O$— | 1 | ⬡ | 0 | — | 0 | — | 1 | 1 | 0 | +3.6° (20° C.) c = 1, $CH_2Cl_2$ | Cryst. $\xrightarrow{65.7}_{54.6}$ SmC* $\xrightarrow{75.8}_{73.1}$ SmA $\xrightarrow{82.5}_{79.9}$ Ch $\xrightarrow{88.5}_{86.1}$ Iso. |
| 19 | $C_4H_9$— | $C_8H_{17}O$— | 1 | ⬡ | 0 | — | 0 | — | 1 | 1 | 0 | −0.6° (28° C.) c = 1, benzene | Cryst. $\xrightarrow{64}_{18}$ SmA $\xrightarrow{75}_{70}$ Ch $\xrightarrow{81}_{79}$ Iso., Sm3 $\xrightarrow{31}$ SmC* $\xrightarrow{47}$ |
| 20 | $C_5H_{11}$— | $C_8H_{17}O$— | 1 | ⬡ | 0 | — | 0 | — | 1 | 1 | 0 | +2.1° (23° C.) c = 5, $CH_2Cl_2$ | Cryst. $\xrightarrow{65}_{51}$ SmA $\xrightarrow{80}_{78}$ Ch $\xrightarrow{87}_{85}$ Iso., SmC* $\xrightarrow{66}$ |
| 21 | $C_4H_9$— | $C_{10}H_{21}O$— | 1 | ⬡ | 0 | — | 0 | — | 1 | 1 | 0 | −1.43° (28° C.) c = 1, benzene | Cryst. $\xrightarrow{73}_{38}$ SmA $\xrightarrow{82}_{80}$ Iso., Sm3 $\xrightarrow{47}$ |

TABLE 1-continued

| Example | R | R¹ | l | A | m | B | n | C | p | q | r | Optical rotation $[\alpha]_D$ | Phase transition temperature (°C.) |
|---|---|---|---|---|---|---|---|---|---|---|---|---|---|
| 22 | $C_6H_{13}-$ | $C_{10}H_{21}O-$ | 1 | ⬡ (benzene) | 0 | — | 0 | — | 1 | 1 | 0 | −2.2° (23° C.) c = 1, benzene | Cryst. ⇌75⇌ SmC* ⇌83⇌81 SmA ⇌90⇌88 Iso. / 54 ↘ 45 Sm3 |
| 23 | $C_6H_{13}-$ | $C_6H_{13}O-$ | 1 | ⬡ | 0 | — | 0 | — | 1 | 1 | 0 | −1.6° (28° C.) c = 1, benzene | Cryst. ⇌74.5⇌ Ch. ⇌86⇌85.5 Iso. / 60.4 ↘ 51.0 SmC* |
| 24 | $C_6H_{13}-$ | $C_8H_{17}O-$ | 2 | ⬡ | 0 | — | 0 | — | 0 | 0 | 0 | 0 | Cryst. ⇌116⇌112 Iso. |
| 25 | $C_8H_{17}-$ | $C_{10}H_{21}-$ | 1 | ⬡(N,N pyridine) | 1 | ⬡ | 0 | — | 0 | 0 | 0 | 0 | Cryst. ⇌66⇌58 SmC* ⇌70⇌69 SmA ⇌72⇌71 Iso. |
| 26 | $C_8H_{17}-$ | $C_9H_{19}-$ | 1 | ⬡(N,N) | 1 | ⬡ | 0 | — | 0 | 0 | 0 | 0 | Cryst. ⇌74.0⇌70.0 Iso. |
| 27 | $C_6H_{13}-$ | $C_{10}H_{21}-$ | 1 | ⬡(N,N) | 1 | ⬡ | 0 | — | 0 | 0 | 0 | 0 | Cryst. ⇌58⇌ SmC* ⇌61⇌60 SmA ⇌70⇌68 Iso. / 45 ↘ 22 Sm3 |
| 28 | $C_5H_{11}-$ | $C_6H_{13}O-$ | 1 | ⬡ | 0 | — | 0 | — | 1 | 1 | 0 | +1.4° (22° C.) c = 5, $CH_2Cl_2$ | Cryst. ⇌58⇌ Ch. ⇌83⇌82 Iso. / 50 ↘ 45 SmC* |

TABLE 1-continued

| Example | R | R¹ | l | A | m | B | n | C | p | q | r | Optical rotation $[\alpha]_D$ | Phase transition temperature (°C) |
|---|---|---|---|---|---|---|---|---|---|---|---|---|---|
| 29 | $C_8H_{17}$— | $C_7H_{15}O$— | 1 | (phenyl) | 0 | — | 0 | — | 1 | 1 | 0 | | Cryst. ⇌79 Ch. ⇌85/84 Iso.; Ch. →75 SmC*; SmC* →54 Cryst. |
| 30 | $C_8H_{17}$— | $C_6H_{13}O$— | 1 | (phenyl) | 0 | — | 0 | — | 1 | 1 | 0 | | Cryst. ⇌78.2 Ch. ⇌86.0 Iso.; Ch. →69.0 SmC*; SmC* →58 Cryst. |
| 31 | $C_6H_{13}$— | $C_7H_{15}O$— | 1 | (phenyl) | 0 | — | 0 | — | 1 | 1 | 0 | | Cryst. ⇌76 Ch. ⇌86/85 Iso.; Ch. →70 SmC*; SmC* →53 Cryst. |

The liquid crystal composition according to the present invention contains at least one species of the fluoroalkane derivative represented by the formula (I). For example, the fluoroalkane derivative represented by the formula (I) may be mixed with a ferroelectric liquid crystal selected from those of the formulas (1)–(13) shown below to increase the spontaneous polarization and increase the response speed. In this case, it is preferred to use the fluoroalkane derivative represent by the formula (I) in an amount constituting 0.1–99 wt. %, particularly 1–90 wt. % of the resulting liquid crystal composition.

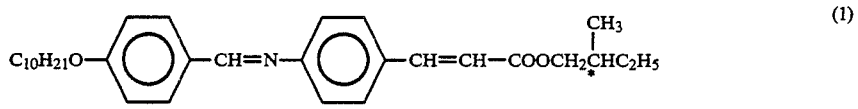
(1)

p-decyloxybenzylidene-p'-amino-2-methylbutylcinnamate (DOBAMBC)

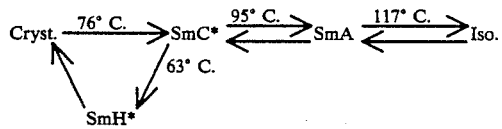

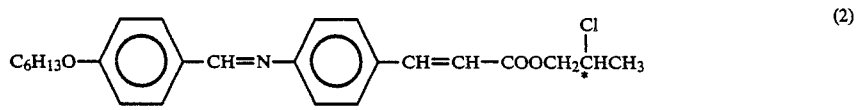
(2)

p-hexyloxybenzylidene-p'-amino-2-chloropropylcinnamate (HOBACPC)

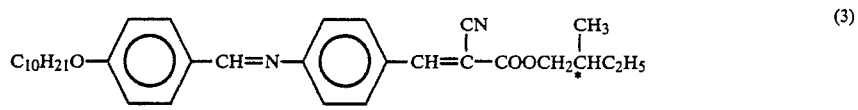
(3)

p-decyloxybenzylidene-p'-amino-2-methylbutyl-α-cyanocinnamate (DOBAMBCC)

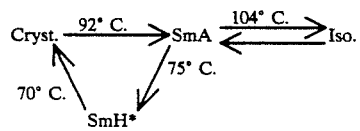

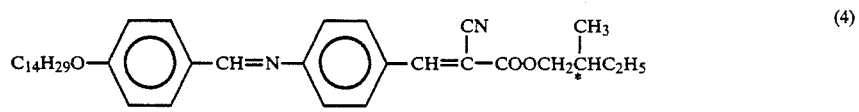
(4)

p-tetradecyloxybenzylidene-p'-amino-2-methylbutyl-α-cyanocinnamate (TDOBAMBCC)

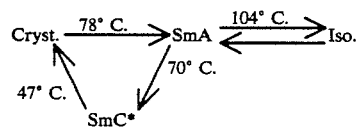

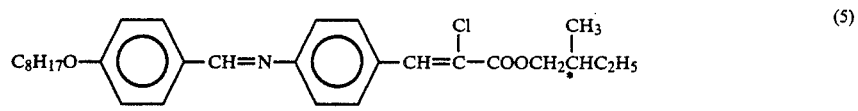
(5)

p-octyloxybenzylidene-p'-amino-2-methylbutyl-α-chlorocinnamate (OOBAMBCC)

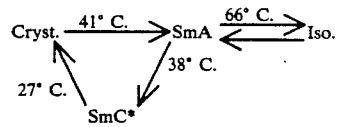

-continued

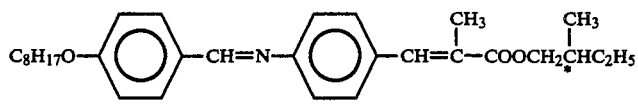 (6)

p-octyloxybenzylidene-p'-amino-2-methylbutyl-α-methylcinnamate

Cryst. ⇌49° C. SmC* ⇌58° C. SmA ⇌94° C. Iso.

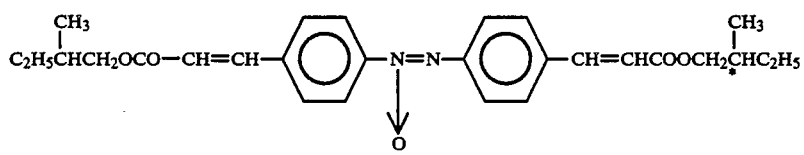 (7)

4,4'-azoxycinnamic acid-bis(2-methylbutyl)ester

Cryst. ⇌121° C. SmC* ⇌134° C. SmA ⇌168° C. Iso.

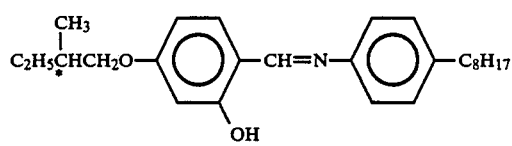 (8)

4-O—(2-methylbutyl)resorcylidene-4'-octylaniline

Cryst. ⇌28° C. SmC* ⇌55° C. SmA ⇌62° C. Iso.

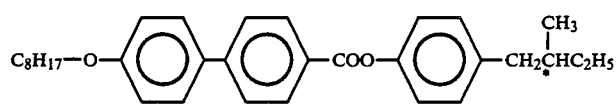 (9)

4-(2'-methylbutyl)phenyl-4'-octyloxybiphenyl-4-carboxylate

Cryst. ⇌78° C. Sm3 ⇌80° C. SmC* ⇌128.3° C. SmA ⇌171.0° C. Ch ⇌174.2° C. Iso.

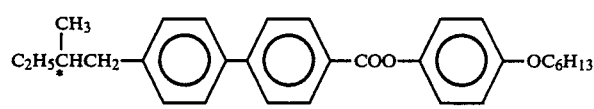 (10)

4-hexyloxyphenyl-4-(2''-methylbutyl)biphenyl-4'-carboxylate

Cryst. ⇌68.8° C. SmC* ⇌80.2° C. Ch. ⇌163.5° C. Iso.

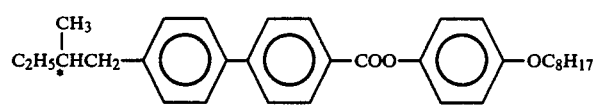 (11)

4-octyloxyphenyl-4-(2''-methylbutyl)biphenyl-4'-carboxylate

Cryst. ⇌76° C. SmC* ⇌88.6° C. Ch ⇌155.4° C. Iso.

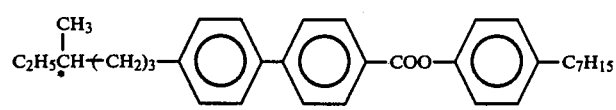 (12)

4-hexyloxyphenyl-4-(2''-methylbutyl)biphenyl-4'-carboxylate

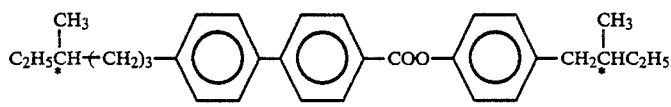

4-(2''-methylbutyl)phenyl-4-(4''-methylhexyl)biphenyl-4'-carboxylate

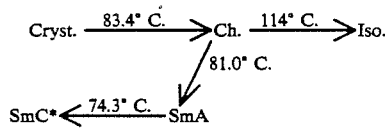

The fluoroalkane derivative represented by the formula (I) may also be mixed with a smectic liquid crystal such as those of the formula (1)–(5) below which per se are not chiral to provide a composition which may be used as a ferroelectric liquid crystal. In this case, the fluoroalkane derivative represented by the formula (I) may preferably be used in an amount of 0.1–99 wt. %, particularly 1–90 wt. %. The resultant composition may be provided with an increased spontaneous polarization corresponding to the content of a fluoroalkane derivative according to the present invention.

(1)

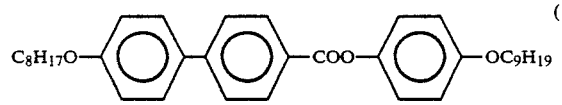

(4-nonyloxyphenyl)-4'-octyloxybiphenyl-4-carboxylate

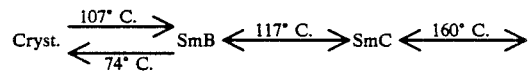

(2)

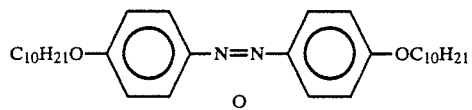

4,4'-decyloxyzaoxybenzene

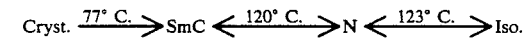

(3)

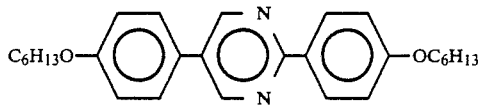

2-(4'-hexyloxyphenyl)-5-(4-hexyloxyphenyl)-pyrimidine

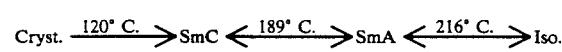

(4)

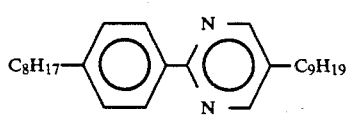

2-(4'-octyloxyphenyl)-5-nonylpyrimidine

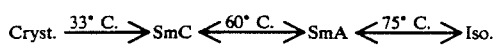

-continued (5)

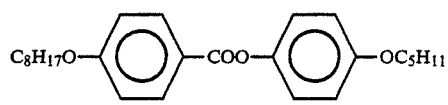

4'-pentyloxyphenyl-4-octylazoxybenzoate

The present invention will be explained more specifically with reference to some examples.

EXAMPLE 1

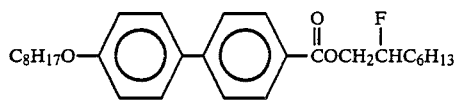

2-Fluorooctyl p-octyloxybiphenylcarboxylate represented by the above formula was produced through the following reaction scheme:

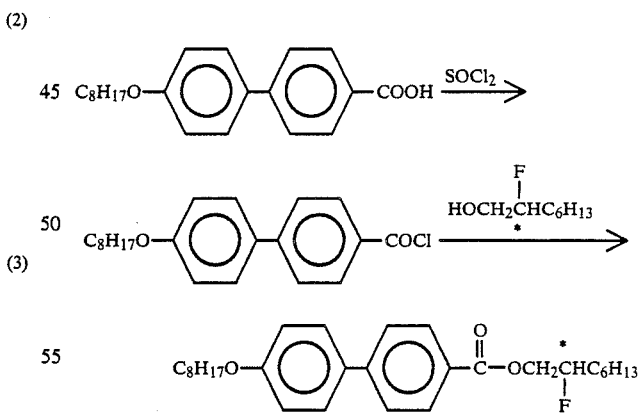

More specifically, 0.74 g (2.3 mmol) of p-octyloxybiphenylcarboxylic acid and 5 ml of thionyl chloride were subjected to heat-refluxing for 2.5 hours, followed by removal of unreacted thionyl chloride by distillation to obtain a corresponding acid chloride.

Separately, 0.50 g (4.5 mmol) of triethylenediamine was dissolved in 5 ml of dry benzene, and potassium chloride was added thereto for drying for about 30 min. The solution was charged in a vessel containing 0.40 g (2.7 mmol) of (−)-2-fluorooctanol, followed by stirring under vibration. The solution was added dropwise into the above acid chloride under stirring, and the mixture was then further stirred at 50° C. for 2 hours.

After the completion of the reaction, 1N-hydrochloric acid and water were added thereto, followed by extraction with benzene. Into the benzene layer, a 1N-sodium carbonate aqueous solution was added, and further benzene-extraction was conducted. The resultant benzene solution was charged with anhydrous sodium sulfate for drying overnight.

After distilling-off of the benzene, the residue was separated by silica gel column chromatography with the use of a benzene/hexane (1/1) mixture as an eluent to obtain 0.53 g (yield: 50%) of 2-fluorooctyl p-octyloxybiphenylcarboxylate.

The following optical rotation and IR (infrared absorption) data were obtained.

Optical rotation: $[\alpha]_D^{26.4} + 13.1°$ (c=2, benzene). IR (cm$^{-1}$): 2900 1715, 1605, 1300, 1200, 1120, 830, 770.

EXAMPLES 2, 5 AND 13

Example 1 was repeated except that p'-octyloxybiphenylcarboxylic acid and 2-fluoro-1-octanol were replaced by a carboxylic acid providing groups $R^1$,

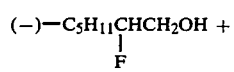

l, m and n and a 2-fluoro-1-alkanol providing a group R, respectively indicated in the above mentioned Table 1, whereby fluoroalkane derivatives shown in the Table 1 according to the present invention were respectively obtained.

The optical rotations and phase-transition temperature data of the obtained products were also shown in Table 1 together with those obtained in Example 1.

EXAMPLE 3

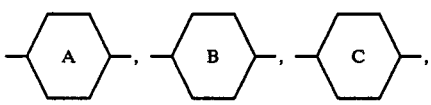

5-Octyloxy-2-[4-(2-fluoroheptyloxy)phenyl]-pyrimidine shown above was produced according to the following scheme:

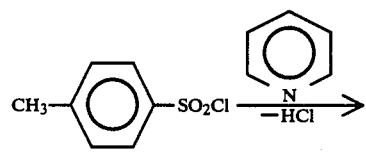

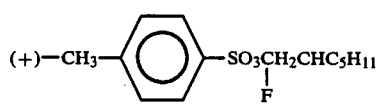

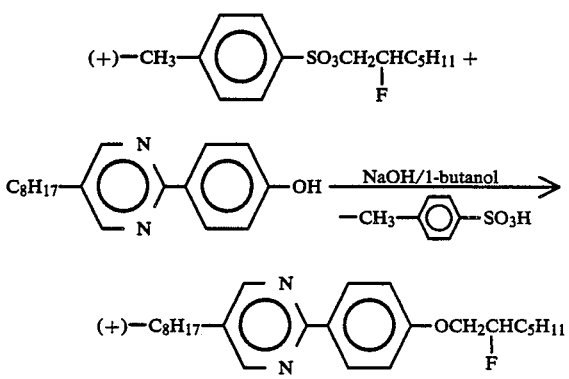

Into a sufficiently nitrogen-substituted vessel, 0.40 g (3.0 mmol) of (−)-2-fluoroheptanol and 1.00 g (13 mmol) of dry pyridine were charged and stirred under cooling with ice for 30 min. The solution was charged with 0.69 g (3.6 mmol) of p-toluenesulfonic acid chloride and further stirred for 5 hours. After the reaction, 10 ml of 1N-HCl was added, followed by two times of extraction with 10 ml of methylene chloride. Then, the extract liquid was once washed with 10 ml of distilled water. The resultant methylene chloride solution was dried with anhydrous sodium sulfate added in an appropriate amount, and the solvent was distilled off to obtain 0.59 g (2.0 mmol) of (+)-2-fluoroheptyl p-toluenesulfonate at a yield of 66%.

The optical rotation and IR data of the product were as follows:

Optical rotation $[\alpha]_D^{26.4} + 2.59°$ (c=1, CHCl$_3$).
Optical rotation $[\alpha]_{435}^{23.6} + 0.58°$ (c=1, CHCl$_3$).
IR (cm$^{-1}$): 2900, 2850, 1600, 1450, 1350, 1170, 1090, 980, 810, 660, 550.

To 0.43 g (1.5 mmol) of the (+)-2-fluoroheptyl p-toluenesulfonate obtained above and 0.28 g (1.0 mmol) of 5-octyl-2-(4-hydroxyphenyl)pyrimidine, 0.2 ml of 1-butanol was added, and they were sufficiently stirred. To the resultant solution was quickly added an alkalline solution which was prepared in advance by dissolving 0.048 g (1.2 mmol) of sodium hydroxide in 1.0 ml of 1-butanol, and the mixture was heat-refluxed for 5.5 hours. After the reaction, 10 ml of distilled water was added, followed by one time each of extraction with 10 ml and 5 ml of benzene. The extract liquid was dried with an appropriate amount of anhydrous sodium sulfate. After the drying, the solvent was distilled off, and the residue was subjected to silica gel column chromatography with chloroform, thereby to obtain 0.17 g (0.43 mmol) of (+)-5-octyl-2[4-(2-fluoroheptyloxy)-phenyl]pyrimidine at a yield of 43%.

The product showed the following optical rotation and IR data:

Optical rotation $[\alpha]_D^{25.6} + 0.44°$ (c=1, CHCl$_3$).
Optical rotation $[\alpha]_{435}^{22.4} + 4.19°$ (C=1, CHCl$_3$).
IR (cm$^{-1}$): 2900, 2850, 1600, 1580, 1420, 1250, 1160, 800, 720, 650, 550.

EXAMPLES 4, 24, 25, 26 AND 27

Example 3 was repeated except that 2-fluoroheptanol and 5-octyl-2-(4-hydroxyphenyl)pyrimidine were replaced by a 2-fluoro-1-alkanol providing a R and a 4-substituted phenol derivative providing groups $R^1$,

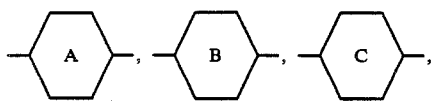

l, m and n, respectively indicated in the above mentioned Table 1, whereby fluoroalkane derivatives shown in the Table 1 according to the present invention were respectively obtained.

EXAMPLE 7

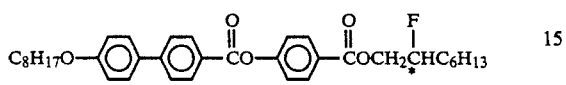

P"-(2-fluorooctyloxycarbonyl)phenyl P'-octyloxybiphenylcarboxylate shown above was produced through the following reaction steps (1), (2) and (3).

(1) Production of 2-fluorooctyl p-acetyloxybenzoate:

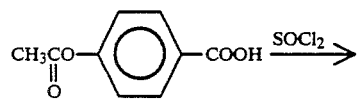

1

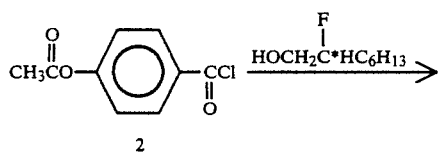

2

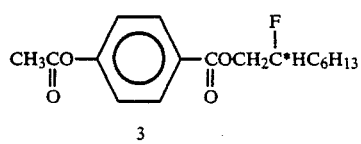

3

0.68 g (3.7 mmol) of p-acetoxybenzoic acid (the above 1) was heat-refluxed together with 7 ml of thionyl chloride for 2.5 hours, followed by removal of unreacted thionyl chloride to obtain a corresponding acid chloride.

Separately, 0.83 g (7.4 mmol) of triethylenediamine was dissolved in 5 ml of dry benzene, and potassium chloride was added thereto to effect drying for about 30 min. The solution was charged in a vessel containing 0.66 g (4.5 mmol) of (−)-2-fluoro-1-octanol, followed by stirring under vibration. The solution was added dropwise into the above acid chloride under stirring, and the mixture was further stirred at 50° C. for 2 hours.

After the reaction, 8 ml of 1N-HCl and 30 ml of water were added, followed by extraction with benzene. The aqueous layer was further subjected to two times of extraction with 8 ml of benzene. To the benzene layer, 15 ml of 1N-sodium carbonate was added, and further subjected to extraction with water similarly as above, followed by two times of extraction of the water layer with 8 ml of benzene. The benzene layer was charged with anhydrous sodium sulfate for drying overnight.

By distilling off the benzene, a crude product was obtained, which was then subjected to separation by silica gel column chromatography with a benzene:hexane (1:1) mixture, thereby to obtain 0.80 g (yield: 69%) of 2-fluorooctyl p-acetyloxybenzoate.

Optical rotation $[\alpha]_D^{24} + 11.2°$ (c=2, benzene).

IR (cm$^{-1}$):2850–2950, 1760, 1720, 1600, 1265, 1190.

(2) Production of 2-fluorooctyl p-hydroxybenzoate:

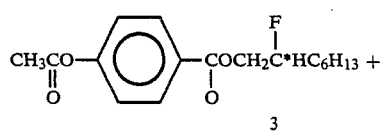

3

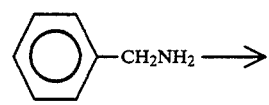

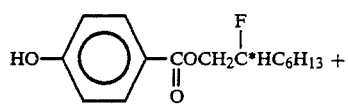

4

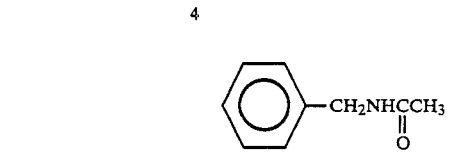

5

0.750 g (2.5 mmol) of the purified product (3) obtained in the above step (1) was dissolved in 1.5 ml of ether. Into the solution, a solution of 0.27 g (2.5 mmol) of benzyl amine in 1.5 ml of ether was added, followed by standing overnight at room temperature.

Thereafter, the ether was distilled off to obtain a mixture of 2-fluorooctyl p-hydroxybenzoate (4) and N-acetylbenzylamine (5). The mixture was separated by silica gel column chromatography with a mixture liquid of ethyl acetate:methylene chloride (=1:9), thereby to obtain 0.53 g of 4 in purified form (yield: 78 %). The optical rotation and IR data of the product were as follows:

Optical rotation $[\alpha]_D^{27.6} + 12.6°$ (c=2, benzene).

IR (cm$^{-1}$): 3390, 2850–2940, 1675, 1605, 1590, 1265.

(3) Production of p"-(2-fluorooctyloxycrrbonyl)phenyl p'-octyloxybiphenylcarboxylate:

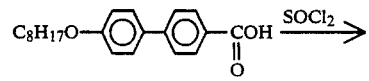

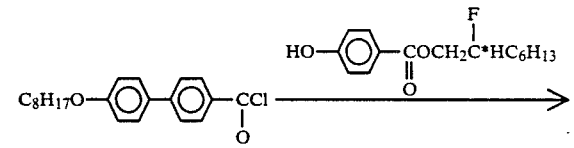

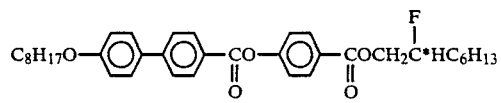

0.65 g (2 mmol) of p'-octyloxybiphenylcarboxylic acid was heat-refluxed together with 4 ml of thionyl chloride for 2.5 hours, followed by removal of unreacted thionyl chloride to obtain a corresponding acid chloride.

Separately, 0.44 g (4 mmol) of triethylenediamine was dissolved in 5 ml of dry benzene, and potassium hydroxide was added thereto to effect drying for about 30 min. The resultant solution was charged in a vessel containing 0.53 g (2 mmol) of the 2-fluorooctyl p-hydroxybenzoate, followed by stirring under vibration. The solution was added dropwise into the above acid chloride under stirring, and the mixture was further stirred at 50° C. for 2 hours.

After the reaction, 1N-HCl and water were added, followed by extraction with benzene, addition of 1N-sodium carbonate aqueous solution and extraction with benzene. The benzene solution was charged with anhydrous sodium sulfate for drying overnight.

After distilling off the benzene, the residual product was separated by silica gel chromatography with benzene as an eluent, thereby to obtain 0.58 g of p''-(2-fluorooctyloxycarbonyl)phenyl p'-octyloxybiphenyl-carboxylate. The optical rotation and IR data of the product were as follows:

Optical rotation $[\alpha]_D^{26.4} +8.7°$ (c=2, benzene).

IR (cm$^{-1}$): 2950–2850, 1740, 1730, 1610, 1295, 1285, 1120, 1080, 830, 760.

EXAMPLES 6, 12 AND 16

Example 7 was repeated except that p-acetoxybenzoic acid, 2-fluoro-1-octanol and p'-octyloxybiphenyl-carboxylic acid were replaced by a carboxylic acid providing groups p, q and r, a 2-fluoro-1-alkanol providing a group R, and a carboxylic acid providing groups $R^1$,

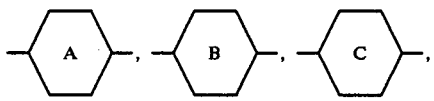

l, m and n, respectively indicated in the above mentioned Table 1, whereby fluoroalkane derivatives shown in the Table 1 according to the present invention were respectively obtained. The optical rotations and phase-transition temperature data of the obtained products were also shown in Table 1 together with those obtained in Example 7.

EXAMPLE 11

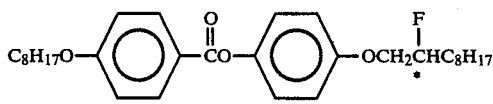

P'-2-fluorodecyloxyphenyl p-octyloxybenzoate was produced through the following reaction steps (1) and (2).

(1) Production of p-hydroquinone mono(2-fluorodecyl)ether:

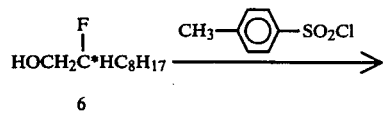

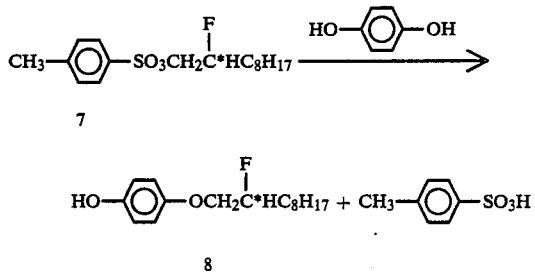

3.15 g (18 mmol) of 2-fluorodecanol (6) and 4.25 g (54 mmol) of dry pyridine together charged in a vessel with a nitrogen atmosphere and stirred. The vessel was then cooled with ice, and 3.75 (20 mmol) of p-toluenesulfonyl chloride was added thereto half by half in two times, followed by stirring for 3 hours. After the reaction, the reaction product was neutralized with hydrochloric acid and subjected to extraction with 10 ml of methylene chloride. The water layer was further extracted two times with 5 ml of methylene chloride. Water was added to the methylene chloride, followed further by extraction with methylene chloride. The resultant methylene chloride solution was charged with anhydrous sodium sulfate and dried overnight.

By distilling off the methylene chloride, 5.60 g (yield: 94 %) of 2-fluorodecyl p-toluenesulfonate (7) was obtained. The optical rotation and IR data were as follows:

Optical rotation $[\alpha]_D^{22.0} +4.2°$ (c=2, CHCl$_2$).

IR (cm$^{-1}$): 2850–2900, 1600, 1350, 1170, 1100, 660, 550.

5.60 g (17 mmol) of the above product 7, 3.74 g (34 mmol) of hydroquinone and 5 ml of 1-butanol were mixed under stirring. Into the mixture, a solution of 1.02 g (25 mmol) of sodium hydroxide in 13 ml of 1-butanol was gradually added, followed by reaction at 130° C. for 7 hours. After the reaction, 40 ml of water was added, followed by extraction with ether. The resultant ether solution was charged with anhydrous sodium sulfate and dried overnight. After distilling off the solvent, the residue was subjected to separation by silica gel column chromatography with methylene chloride, thereby to obtain 2.57 g (yield: 56%) of purified p-hydroquinone mono(2-fluorodecyl)ether (8). The optical rotation and IR data of the product were as follows.

Optical rotation $[\alpha]_D^{24.0} +1.8°$ (c=2, CHCl$_2$).

IR (cm$^{-1}$): 3600–3200, 2900, 1680, 1590, 1280, 1160, 700.

(2) Production of p'-(2-fluorodecyloxy)phenyl p-octyloxybenzoate:

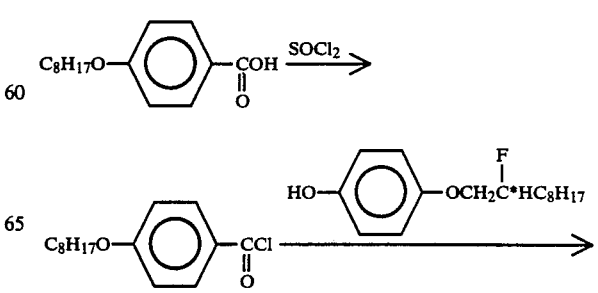

0.93 g (3.7 mmol) of p-octyloxybenzoic acid was heat-refluxed together with 8 ml of thionyl chloride for 2 hours, followed by distilling-off of unreacted thionyl chloride to obtain a corresponding acid chloride.

Separately, 0.81 g (7,4 mmol) of triethylenediamine was dissolved in dry benzene, and potassium hydroxide was added thereto to effect drying for about 30 min. The resultant solution was charged in a vessel containing 1.0 g (3.7 mmol) of p-hydroquinone mono(2-fluorodecyl)ether obtained in the above step (1), followed by stirring under vibration. The solution was added dropwise into the above acid chloride under stirring, and the mixture was further heated at 50° C. for 2 hours.

After the reaction, 1N-HCl and water were added, followed by extraction with benzene, addition of 1N-sodium carbonate aqueous solution and extraction with benzene. The benzene solution was charged with anhydrous sodium sulfate for drying overnight.

After distilling off the benzene, the residual product was separated by silica gel chromatography with benzene as an eluent, thereby to obtain 1.49 g (yield: 81%) of p'-(2-fluorodecyloxy)phenyl p-octyloxybenzoate. The optical rotation and IR data of the product were as follows:

Optical rotation $[\alpha]_D^{23.2}$ −1.5° (c=2, benzene).

IR (cm$^{-1}$): 2900, 1,40, 1610, 1520, 1280, 1250, 1210, 1170, 1130, 760, 690.

EXAMPLES 8, 9, 10, 14, 17, 18, 19, 20, 21, 22, 23 28, 29, 30 AND 31

Example 11 was repeated except that 2-fluorodecanol, p-hydroquinone and p-octyloxybenzoic acid were replaced by a 2-fluoro-1-alkanol providing R, p-hydroquinone or p,p'-dihydroxybiphenyl, and a carboxylic acid providing groups R$^1$, l, m and n, respectively indicated in the above mentioned Table 1, whereby fluoroalkane derivatives shown in the Table 1 according to the present invention were respectively obtained.

The optical rotations and phase-transition temperature data of the obtained products were also shown in Table 1 together with those obtained in Example 11.

EXAMPLE 32

A liquid crystal composition containing a mesomorphic compound (2-fluorooctyl p-octyloxybiphenylcarboxylate) was prepared as shown below together with the phase transition temperatures.

$C_8H_{17}O$—⬡—⬡—COCH$_2$C*HC$_6$H$_{13}$  13.3 wt. %

MORA-8

$C_2H_5C^*H$(CH$_3$)(CH$_2$)$_5$—⬡(OH)—CH=N—⬡—$C_8H_{17}$  86.7 wt. %

Cryst. ←−21° C.− SmC* ←81° C.− Iso.

The composition showed a spontaneous polarization of 8.8 nC/cm$^2$ which is about 8 times 0.45 nC/cm$^2$, the spontaneous polarization of MORA 8 alone.

EXAMPLE 33

A liquid crystal device was prepared by using a mesomorphic compound prepared in Example 11.

A 1000 Å-thick ITO film was applied to form electrodes onto a highly polished glass substrate of 10×20 mm in size, and an about 1000 Å-thick SiO$_2$ layer was deposited thereon by the ion beam process. On one of the thus tread pair of glass substrates, the mesomorphic compound (p'-(2-fluorodecyloxy)phenyl p-octyloxybenzoate) prepared in Example 11 was dropped, and the other substrate was superposed thereon. The substrates were held at 80° C. and mutually slided in a parallel movement while maintaining a spacing therebetween at 1.2 μm and observed through a polarizing microscope, whereby a homogeneously aligned monodomain having lost spiral structure was observed to be formed. In this state, pulses of ±10 volts with a duration of 200μsec were applied at 65° C., whereby satisfactory switching was effected with a contrast of 18.

What is claimed is:

1. A fluoroalkane derivative represented by the formula:

R—(A)$_l$—(B)$_m$—(C)$_n$—COO—(⬡)$_{q/p}$—CO$_r$—OCH$_2$C*HR$_1$   (I)
              F wherein R denotes an alkyl group having 1–16 carbon atoms, C* denotes an asymmetric carbon atom, R$^1$ denotes an alkyl or alkoxy group having 1–16 carbon atoms;

—(A)—, —(B)— and —(C)— respectively denote a phenylene group

—(⬡)—, a cyclohexylene group

—(H)— or a pyrimidinylene group

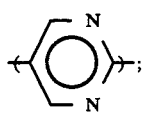

p is 0 or 1, q is 1 or 2 when p is 1, r is 0 or 1; and l, m and n are respectively 0 or a positive integer satisfying the relationship of $l+m+n \geq 1$.

2. A fluoroalkane derivative according to claim 1, which is a compound showing a liquid crystal phase.

3. A fluoralkane derivative according to claim 2, which shows cholesteric phase, smectic A phase, and chiral smectic C phase.

4. A fluoroalkane derivative according to claim 2, which shows cholesteric phase and chiral smectic C phase.

5. A fluoroalkane derivative according to claim 2, which shows smectic A phase and chiral smectic C phase.

6. A fluoroalkane derivative according to claim 1, wherein the symbols in the formula (I) are respectively as follows; R: $C_6H_{13}$—, $R^1$: $C_8H_{17}O$—, l: 2,

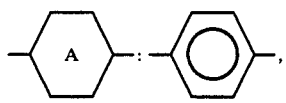

m: 0, n: 0, p: 0 and r: 1.

7. A fluoralkane derivative according to claim 1, wherein the symbols in the formula (I) are respectively as follows; R: $C_6H_{13}$—, $R^1$: $C_{10}H_{21}O$—, l: 2,

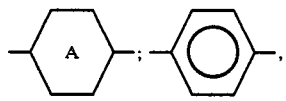

m: 0, n:0, p: 0 and r: 1.

8. A fluoroalkane derivative according to claim 1, wherein the symbols in the formula (I) are respectively as follows; R: $C_5H_{11}$—, $R^1$: $C_8H_{17}$, l: 1,

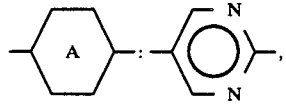

m: 1, B:

n: 0, p: 0 and r: 0.

9. A fluoralkane derivative according to claim 1, wherein the symbols in the formula (I) are respectively as follows; R: $C_6H_{13}$—, $R^1$: $C_8H_{17}$, l: 1,

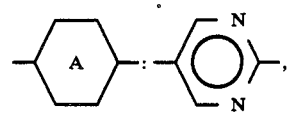

m: 1,

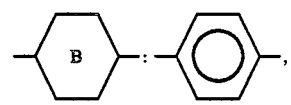

n: 0, p: 0 and r: 0.

10. A fluoroalkane derivative according to claim 1, wherein the symbols in the formula (I) are respectively as follows; R: $C_8H_{17}$—, $R^1$: $C_7H_{15}$—, l: 1,

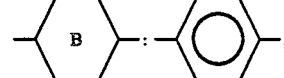

m: 1,

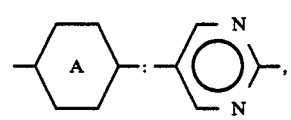

n: 0, p: 0 and r: 1.

11. A fluoroalkane derivative according to claim 1, wherein the symbols in the formula (1) are respectively as follows; R: $C_7H_{15}$—, $R^1$: $C_{10}H_{21}O$—, l: 2,

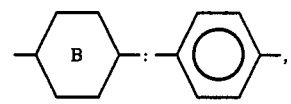

m: 0, n: 0, p: 1, q: 1 and r: 1.

12. A fluroalkane derivative according to claim 1, wherein the symbols in the formula (I) are respectively as follows; R: $C_6H_{13}$—, $R^1$: $C_8H_{17}O$—, l: 2,

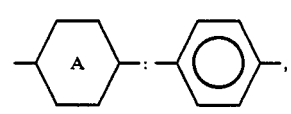

m: 0, n: 0, p: 1, q: 1 and r: 1.

13. A fluoralkane derivative according to claim 1, wherein the symbols in the formula (I) are respectively as follows; R: $C_8 H_{17}$—, $R^1$: $C_7H_{15}$—, l: 1,

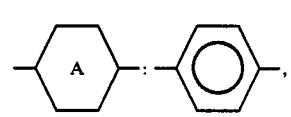

m:1,

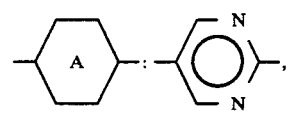

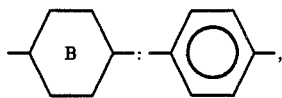

n: 0, p: 1, q: 1 and r: 0.

14. A fluoralkane derivative according to claim 1, wherein the symbols in the formula (I) are respectively as follows; R: $C_8H_{17}$—, $R^1$: $C_{10}H_{21}O$—, 1: 2,

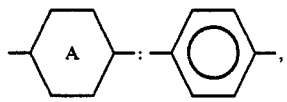

m: 0, n: 0, p: 1, q: 11 and r: 0.

15. A fluoralkane derivative according to claim 1, wherein the symbols in the formula (I) are respectively as follows; R: $R_6H_{13}$—, $R^1$: $C_8H_{17}O$—, 1: 1,

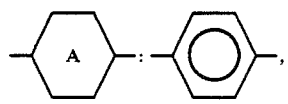

m: 0, n: 0, p: 1, q: 2 and r: 0.

16. A fluoralkane derivative according to claim 1, wherein the symbols in the formula (I) are respectively as follows; R: $C_8H_{17}$—, $R^1$: $C_8H_{17}O$—, 1: 1,

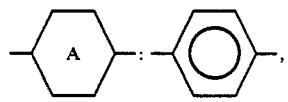

m: 0, n: 0, p: 1, q: 1 and r: 0.

17. A fluoralkane derivative according to claim 1, wherein the symbols in the formula (I) are respectively as follows; R: $C_8H_{17}$—, $R^1$: $C_8H_{17}O$—, 1: 1,

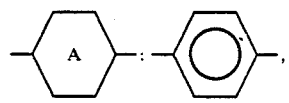

m: 0, n: 0, p: 1, q: 1 and r: 1.

18. A fluoroalkane derivative according to claim 1, wherein the symbols in the formula (1) are respectively as follows; R: $C_8H_{17}$—, $R^1$: $C_7H_{15}$—, 1: 1,

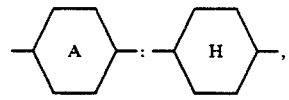

m:1,

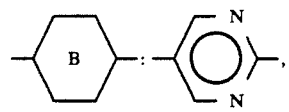

n: 1,

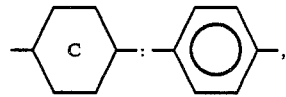

n: 0, q: 0 and r: 1.

19. A fluoralkane derivative according to claim 1, wherein the symbols in the formula (I) are respectively as follows; R: $C_6H_{13}$—, $R^1$: $C_{12}H_{25}O$—, 1: 1,

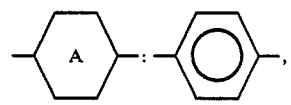

m: 0, n: 0, p: 1, q: 1 and r: 0.

20. A fluoralkane derivative according to claim 1, wherein the symbols in the formula (I) are respectively as follows; R:$C_{12}H_{25}$, $R^1$: $C_6H_{13}O$—, 1: 1,

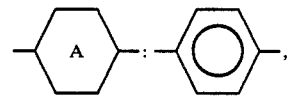

m: 0, n: 0, p: 1, q: 1 and r: 0.

21. A fluoralkane derivative according to claim 1, wherein the symbols in the formula (I) are respectively as follows; R: $C_6H_{13}$—, $R^1$: $C_8H_{17}O$—, 1: 1,

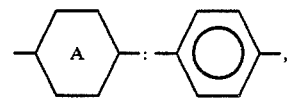

m: 0, n: 0, p: 1, q: 2 and r: 1.

22. A fluoralkane derivative according to claim 1, wherein the symbols in the formula (I) are respectively as follows; R:$C_5H_{11}$—, $R^1$: $C_{10}H_{21}O$—, 1: 1,

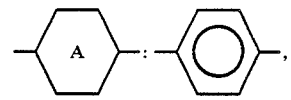

m: 0, n: 0, p: 1, q: 1 and r: 0.

23. A fluoralkane derivative according to claim 1, wherein the symbols in the formula (I) are respectively as follows R: $C_6H_{13}$—, $R^1$: $C_8H_{17}O$—, 1: 1,

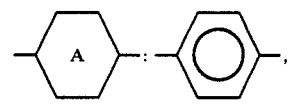

m: 0, n: 0, p: 1, q: 1 and r: 0.

24. A fluoralkane derivative according to claim 1. wherein the symbols in the formula (I) are respectively as follows; R: $C_4H_9$—, $R^1$: $C_8H_{17}O$—, 1: 1,

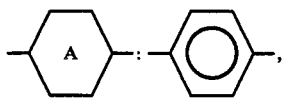

m: 0, n: 0, p: 1, q: 1 and r: 0.

25. A fluoralkane derivative according to claim 1, wherein the symbols in the formula (I) are respectively as follows; R: $C_5H_{11}$—, $R^1$: $C_8H_{17}O$—, l: 1,

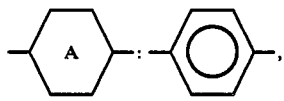

m: 0, n: 0, p: 1, q: 1 and r: 0.

26. A fluoralkane derivative according to claim 1, wherein the symbols in the formula (I) are respectively as follows; R: $C_4H_9$—, $R^1$: $C_{10}H_{21}O$—; l: 1,

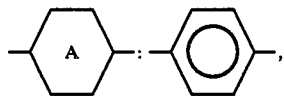

m: 0, n: 0, p: 1, q: 1 and r: 0.

27. A fluoralkane derivative according to claim 1, wherein the symbols in the formula (I) are respectively as follows; R: $C_6H_{13}$—, $R^1$: $C_{10}H_{21}O$—, l: 1,

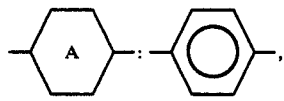

m: 0, n: 0, p: 1, q: 1 and r: 0.

28. A fluoralkane derivative according to claim 1, wherein the symbols in the formula (I) are respectively as follows; R: $C_6H_{13}$—, $R^1$: $C_6H_{13}O$—, l: 1,

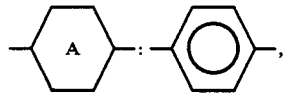

m: 0, n: 0, p: 1, q: 1 and r: 0.

29. A fluoroalkane derivative according to claim 1, wherein the symbols in the formula (I) are respectively as follows; R: $C_6H_{13}$—, $R^1$: $C_8H_{17}O$—, l: 2,

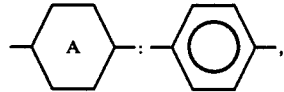

m: 0, n: 0, p: 0 and r: 0.

30. A fluoralkane derivative according to claim 1 wherein the symbols in the formula (I) are respectively as follows; R: $C_8H_{17}$—, $R^1$: $C_{10}H_{21}$—, l: 1,

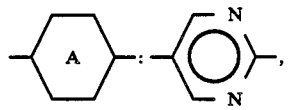

m: 1, n: 0, p: 0 and r: 0.

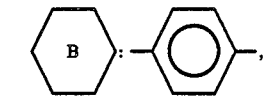

31. A fluoralkane derivative according to claim 1, wherein the symbols in the formula (I) are respectively as follows R: $C_8H_{17}$—, $R^1$: $C_9H_{19}$—, l: 1,

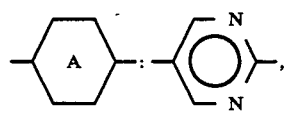

m: 1,

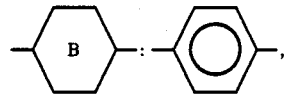

n: 0, p: 0 and r: 0.

32. A fluoralkane derivative according to claim 1, wherein the symbols in the formula (I) are respectively as follows; R: $C_6H_{13}$—, $R^1$: $C_{10}H_{21}$—, l:1

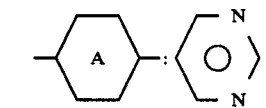

m: 1,

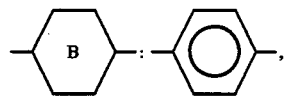

n: 0, p: 0 and r: 0.

33. A fluroalkane derivative according to claim 1, wherein the symbols in the formula (I) are respectively as follows; R: $C_5H_{11}$—, $R^1$: $C_6H_{13}O$—, l: 1,

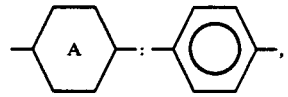

m: 0, n: 0, p: 1, q: 1 and r: 0.

34. A fluoroalkane derivative according to claim 1, wherein the symbols in the formula (I) are respectively as follows; R: $C_8H_{17}$—, $R^1$: $C_7H_{15}O$—, l: 1,

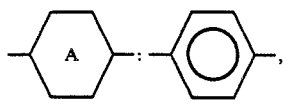

m: 0, n: 0, p: 1, q: 1 and r: 0.

35. A fluoralkane derivative according to claim 1, wherein the symbols in the formula (I) are respectively as follows; R: $C_8H_{17}$—, $R^1$: $C_6H_{13}O$—, l:1,

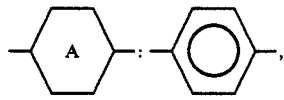

m: 0, n: 0, p; 1, q: 1 and r: 0.

36. A fluoralkane derivative according to claim 1, herein the symbols in the formula (I) are respectively as follows; R: $C_6H_{13}$—, $R^1$: $C_7H_{15}O$—, l: 1,

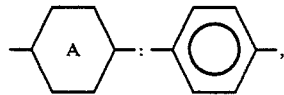

m: 0, n: 0, p: 1, q: 1 r: 0.

37. A liquid crystal composition comprising at least two mesomorphic compounds, at least one of which is a fluoroalkane derivative represented by the formula (I) in claim 1.

38. A composition according to claim 37, which is a ferroelectric liquid crystal composition.

39. A composition according to claim 37, which comprises a combination of the fluoralkane derivative, and a compound showing chiral smectic C phase.

40. A composition according to claim 37, which comprises a combination of the fluoralkane derivative. and a compound showing smectic A phase and smectic C phase.

41. A composition according to claim 37, which comprises a combination of the fluoralkane derivative, and a compound showing cholesteric phase, smectic A phase and chiral smectic C phase.

42. A composition according to claim 37, which comprises a combination of the fluoralkane derivative, and a compound showing cholesteric phase and chiral smectic C phase.

43. A composition according to claim 37, which comprises a combination of the fluoralkane derivative, and a compound showing non-chiral smectic phase.

44. A composition according to claim 37, which contains 0.1–99 wt. % of the fluoroalkane derivative.

45. A composition according to claim 37, which contains 1–90 wt. % of the fluoroalkane derivative.

* * * * *

UNITED STATES PATENT AND TRADEMARK OFFICE
CERTIFICATE OF CORRECTION

PATENT NO. : 4,867,903

DATED : September 19, 1989

INVENTOR(S) : HIROYUKI NOHIRA ET AL.

It is certified that error appears in the above-identified patent and that said Letters Patent is hereby corrected as shown below:

Title page:

AT [56] REFERENCES CITED

Foreign Patent Documents, "87/05012 8/1987 World Int. Prop. O." (second occurrence) should be deleted.

COLUMN 1

Line 12, "devices" should read --device--.

COLUMN 2

Line 25, "derivatives" should read --derivatives.--.
Line 36, "an" should read --a--.
Line 51, "fluoralkane" should read --fluoroalkane--.

COLUMN 3

Line 24, "1+m+n+√1." should read --$1+m+n+\geq 1$.--.

COLUMN 7

Table 1, Example 1, "$C_6H_{13}$—" should read --$C_6H_{12}$---.

UNITED STATES PATENT AND TRADEMARK OFFICE
CERTIFICATE OF CORRECTION

PATENT NO. : 4,867,903
DATED : September 19, 1989
INVENTOR(S) : HIROYUKI NOHIRA ET AL.

It is certified that error appears in the above-identified patent and that said Letters Patent is hereby corrected as shown below:

COLUMN 21

Form (2), "$C_{10}H_{21}O\text{-}\langle\text{phenyl}\rangle\text{-N=N-}\langle\text{phenyl}\rangle\text{-OC}_{10}H_{21}$, with O below" (2)"

should read

-- $C_{10}H_{21}O\text{-}\langle\text{phenyl}\rangle\text{-N=N-}\langle\text{phenyl}\rangle\text{-OC}_{10}H_{21}$, with O below (2)--.

COLUMN 24

Line 67, "a R" should read --a group R--.

COLUMN 26

Line 47, "p"-(2-fluorooctyloxycrrbonyl)phe-" should read --p"-(2-fluorooctyloxycarbonyl)phe---.

COLUMN 28

Line 15, "pyridine" should read --pyridine were--.
Line 33, "(c=2, $CHCl_2$)." should read --(c=2, $CH_2Cl_2$).--.

COLUMN 29

Line 33, "1,40," should read --1740,--.

UNITED STATES PATENT AND TRADEMARK OFFICE
CERTIFICATE OF CORRECTION

PATENT NO. : 4,867,903
DATED : September 19, 1989
INVENTOR(S) : HIROYUKI NOHIRA ET AL.

It is certified that error appears in the above-identified patent and that said Letters Patent is hereby corrected as shown below:

COLUMN 30

Line 5,

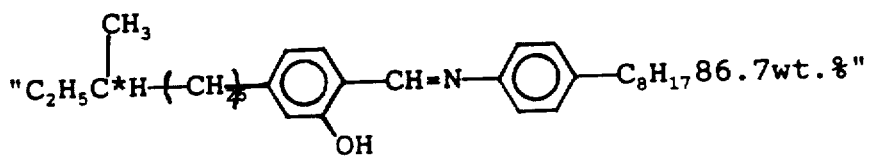

should read

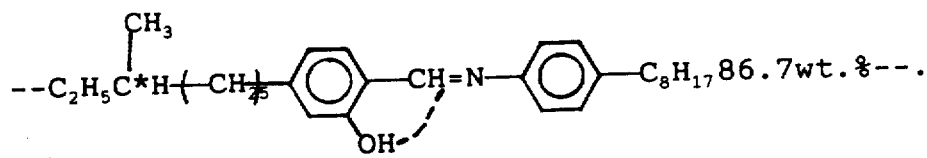

COLUMN 31

Line 15, "fluoralkane" should read --fluoroalkane--.
Line 18, "fluoralkane" should read --fluoroalkane--.
Line 21, "fluoralkane" should read --fluoroalkane--.
Line 25, "fluoralkane" should read --fluoroalkane--.
Line 36, "fluoralkane" should read --fluoroalkane--.
Line 66, "fluoralkane" should read --fluoroalkane--.

COLUMN 32

Line 17, "fluoralkane" should read --fluoroalkane--.
Line 47, "fluoralkane" should read --fluoroalkane--.

UNITED STATES PATENT AND TRADEMARK OFFICE
CERTIFICATE OF CORRECTION

PATENT NO. : 4,867,903
DATED : September 19, 1989
INVENTOR(S) : HIROYUKI NOHIRA ET AL.   Page 4 of 6

It is certified that error appears in the above-identified patent and that said Letters Patent is hereby corrected as shown below:

COLUMN 33

Line 8, "fluoralkane" should read --fluoroalkane--.
Line 18, "q: 11" should read --q: 1--.
Line 19, "fluoralkane" should read --fluoroalkane--.
Line 29, "fluoralkane" should read --fluoroalkane--.
Line 40, "fluoralkane" should read --fluoroalkane--.
Line 52, "formula (1)" should read --formula (I)--.

COLUMN 34

Line 8, "n: 0," should read --p: 0,--.
Line 9, "fluoralkane" should read --fluoroalkane--.
Line 20, "fluoralkane" should read --fluoroalkane--.
Line 31, "fluoralkane" should read --fluoroalkane--.
Line 43, "fluoralkane" should read --fluoroalkane--.
Line 54, "fluoralkane" should read --fluoroalkane--.
Line 56, "follows" should read --follows;--.
Line 65, "fluoralkane" should read --fluoroalkane-- and "claim 1." should read --claim 1,--.

COLUMN 35

Line 9, "fluoralkane" should read --fluoroalkane--.
Line 20, "fluoralkane" should read --fluoroalkane--.
Line 32, "fluoralkane" should read --fluoroalkane--.
Line 43, "fluoralkane" should read --fluoroalkane--.
Line 66, "fluoralkane" should read --fluoroalkane-- and "claim 1" should read --claim 1,--.

UNITED STATES PATENT AND TRADEMARK OFFICE
CERTIFICATE OF CORRECTION

PATENT NO. : 4,867,903
DATED : September 19, 1989
INVENTOR(S) : HIROYUKI NOHIRA ET AL.          Page 5 of 6

It is certified that error appears in the above-identified patent and that said Letters Patent is hereby corrected as shown below:

COLUMN 36

Line 8, "m: 1, n: 0, p: 0 and r: 0."

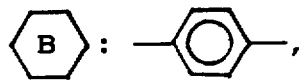

should read
--m: 1,                                --.

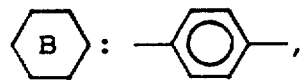

n: 0, p: 0 and r: 0.

Line 16, "fluoralkane" should read --fluoroalkane--.
Line 35, "fluoralkane" should read --fluoroalkane--.
Line 37, "1:1" should read --1: 1,--.
Line 42, "
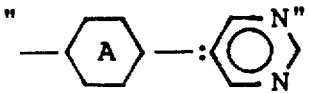

should read
--
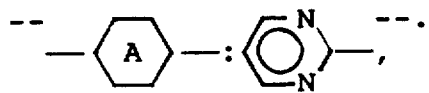
--.

Line 54, "fluoralkane" should read --fluoroalkane--.

COLUMN 37

Line 9, "fluoralkane" should read --fluoroalkane--.
Line 18, "p; 1," should read --p: 1--.
Line 19, "fluoralkane" should read --fluoroalkane--.
Line 20, "herein" should read --wherein--.
Line 29, "q: 1 r:0." should read --q: 1 and r: 0.--.

UNITED STATES PATENT AND TRADEMARK OFFICE
CERTIFICATE OF CORRECTION

PATENT NO. : 4,867,903
DATED : September 19, 1989
INVENTOR(S) : HIROYUKI NOHIRA ET AL.         Page 6 of 6

It is certified that error appears in the above-identified patent and that said Letters Patent is hereby corrected as shown below:

COLUMN 38

Line 8, "fluoralkane" should read --fluoroalkane--.
Line 11, "fluoralkane" should read --fluoroalkane--.

Signed and Sealed this

Seventeenth Day of September, 1991

Attest:

HARRY F. MANBECK, JR.

*Attesting Officer*          *Commissioner of Patents and Trademarks*